(12) United States Patent
Ahn et al.

(10) Patent No.: US 8,702,765 B2
(45) Date of Patent: Apr. 22, 2014

(54) CERVICAL PLATING SYSTEM

(75) Inventors: Sae Young Ahn, Seoul (KR); Hyun Hwa Kwon, Asan-si (KR)

(73) Assignee: Medisourceplus Co., Ltd. (KR)

( * ) Notice: Subject to any disclaimer, the term of this patent is extended or adjusted under 35 U.S.C. 154(b) by 209 days.

(21) Appl. No.: 13/096,594

(22) Filed: Apr. 28, 2011

(65) Prior Publication Data

US 2012/0123475 A1    May 17, 2012

(30) Foreign Application Priority Data

Nov. 12, 2010    (KR) .......................... 10-2010-0112395

(51) Int. Cl.
*A61B 17/80*    (2006.01)

(52) U.S. Cl.
USPC ........................................................ 606/291

(58) Field of Classification Search
USPC .............. 606/280, 286–296; 411/93, 97, 101, 411/102, 116, 122, 123, 235, 533
See application file for complete search history.

(56) References Cited

U.S. PATENT DOCUMENTS 5,607,426 A * 3/1997 Ralph et al. ................... 606/287
6,206,882 B1    3/2001 Cohen

FOREIGN PATENT DOCUMENTS

| EP | 1346697 | 9/2003 |
|---|---|---|
| KR | 10-2007-0072478 | 7/2007 |
| WO | 94/16634 | 8/1994 |

* cited by examiner

*Primary Examiner* — Christian Sevilla
(74) *Attorney, Agent, or Firm* — Cantor Colburn LLP

(57) ABSTRACT

A cervical plating system for fixedly connecting two or more vertebrae to each other includes a cervical plate having a fastening hole, the fastening hole penetrating the cervical plate, a fastening screw fitted into the fastening hole in the cervical plate, and a screw locking member disposed adjacent to the fastening hole. The screw locking member is rotatable along the circumference of the fastening hole between a first position, in which it opens the fastening hole, and a second position, in which it at least partially closes the fastening hole.

23 Claims, 7 Drawing Sheets

CERVICAL PLATING SYSTEM

CROSS REFERENCE TO RELATED APPLICATION

The present application claims priority from Korean Patent Application Number 10-2010-0112395 filed on Nov. 12, 2010, the entire contents of which application are incorporated herein for all purposes by this reference.

BACKGROUND OF THE INVENTION

1. Field of the Invention

The present invention relates to a cervical plating system, and more particularly, to a structure that prevents a fastening screw from being dislodged and fixes the position of the fastening screw in a cervical plating system, which fixedly connects two or more vertebrae to each other.

2. Description of Related Art

Operations and manipulation for treating vertebrae having an affliction, such as intervertebral disk disorders, spinal disc herniation, fractured or dislocated vertebrae, or cervical spondylotic myelopathy, generally include a process of fixing vertebrae by connecting them to each other so that they do not move. In order to fixedly connect two or more vertebrae to each other, a vertebral fixing device or cervical plating system has generally been used from the past.

The vertebral fixing device is an implant that is used for vertebrae, and is generally implanted in the front of the vertebrae from the anterior in order to fixedly connect two or more vertebrae to each other when fusing upper and lower vertebrae. Such a vertebral fixing device is generally a vertebral anterior insert that includes a cervical plate and screws. The operator can fixedly fasten the cervical plate to two or more vertebrae by fitting the screws into holes in the cervical plate and then turning the screws using a tool such as a driver.

Here, when the vertebral fixing device is implanted into the human body, it can be fatal to the patient if a screw becomes dislodged from the cervical plate. Thus, a mechanism that can prevent the screws from being dislodged from the cervical plate is required. According to a mechanism that has generally been used in the related art, an auxiliary plate, which covers the heads of the fastening screws, is fastened to the cervical plate using auxiliary screws.

However, since the auxiliary screws, which fasten the auxiliary plate to the cervical plate, gradually become loose such that they can become dislodged from the cervical plate, the mechanism for preventing the screws from being dislodged in the related art has limited stability and reliability.

In addition, in the state in which the vertebral fixing device is implanted in the human body, even if the fastening screw is not completely dislodged from the cervical plate, the fastening between the vertebrae and the screws may become loose by the influence of vibration from the voice of the patient or the like, so that the fastening screw becomes loose and is not securely fixed. This phenomenon acts as a factor that hinders stable fixing of the vertebrae, and in particular, becomes severe if the fastening screws are fastened in a position in which they are inclined at a predetermined fastening angle instead of being vertically fastened to the vertebrae. Therefore, there are demands for a mechanism for stably fixing the position or posture of the fastening screws fastened to the vertebrae.

The information disclosed in this Background of the Invention section is only for the enhancement of understanding of the background of the invention, and should not be taken as an acknowledgment or any form of suggestion that this information forms a prior art that would already be known to a person skilled in the art.

BRIEF SUMMARY OF THE INVENTION

Various aspects of the present invention provide a cervical plating system designed to fixedly connect two or more vertebrae to each other, and more particularly, a cervical plating system having a structure that can more stably prevent a fastening screw from being dislodged and fixedly connect two or more vertebrae to each other.

In an aspect of the present invention, the cervical plating system for fixedly connecting two or more vertebrae to each other includes a cervical plate having a fastening hole, the fastening hole penetrating the cervical plate, a fastening screw fitted into the fastening hole in the cervical plate, and a screw locking member disposed adjacent to the fastening hole. The screw locking member is rotatable along the circumference of the fastening hole between a first position, in which it opens the fastening hole, and a second position, in which it at least partially closes the fastening hole.

The cervical plating system may also include a screw position fixing member fitted into the fastening hole. The screw position fixing member fixedly surrounds the fastening screw, and is coupled to the screw locking member.

The cervical plate may have a guide recess depressed with respect to the upper surface thereof, the guide recess being formed along the circumference of the fastening hole to guide a rotational movement of the screw locking member.

The cervical plate may further have a fitting recess therein, the screw locking member being fitted into the fitting recess such that a portion of the screw locking member overlaps the fastening hole.

The fitting recess may be configured such that it extends from the guide recess along the circumference of the fastening hole and is depressed in a lateral direction.

The width of the guide recess may be constant along the circumference of the fastening hole, and the width of the fitting recess may gradually decrease in the direction away from the guide recess along the circumference of the fastening hole.

The screw locking member may have a plate like shape, and include a pair of screw locking members, which oppose each other.

The screw locking member may have an inner circumferential surface with a predetermined curvature.

The screw locking member may have a driver socket in the upper surface thereof, such that a driver for rotating the screw locking member fits into the driver socket.

The screw position fixing member may be configured to be movable within a predetermined range in a state in which it is fitted into the fastening hole before the fastening screw is fastened to a vertebra.

The screw position fixing member may be arranged and fixed at an incline in the fastening hole according to a fastening angle of the fastening screw after the fastening screw is fastened to the vertebra.

The screw position fixing member may be shaped as a funnel, with a width thereof gradually decreasing toward bottom, and a portion of the sidewall thereof being open.

The screw locking member may have an inner circumferential surface with a predetermined curvature, and the screw position fixing member may have an outer circumferential surface that couples with the inner circumferential surface of the screw locking member.

The inner circumferential surface of the screw locking member and the outer circumferential surface of the screw position fixing member may be coupled to each other via screw engagement.

The depth to which the guide recess is depressed may be set to be greater than the thickness of the screw locking member.

The inner circumferential surface of the screw locking member may have a curvature that is substantially the same as that of the fastening hole.

The screw locking member may have a circumferential thread line formed in the inner circumferential surface thereof.

The screw locking member may also have an outer circumferential surface that is substantially concentric with the inner circumferential surface.

The thickness of the screw locking member may be relatively thinner than that of the screw locking member.

According to embodiments of the invention, the screw locking member is disposed adjacent to the fastening hole, and is provided along the circumference of the fastening hole such that the screw locking member can rotate between the first position, in which the fastening hole is open, and the second position, in which the fastening hole is at least partially closed. Accordingly, it is possible to more stably and reliably prevent the fastening screw from being dislodged from the cervical plate in the state in which the cervical plating system is implanted into the human body.

In addition, the screw position fixing member is fitted into the fastening hole such that it fixedly surrounds the fastening screw, and is coupled to the screw locking member. Accordingly, it is possible to prevent the phenomenon in which the fastening between a vertebra and a screw becomes loose so that the vertebra is not stably fixed in the event that the fastening screw is shaken, even if the fastening screw is not completely dislodged from the cervical plate.

BRIEF DESCRIPTION OF THE DRAWINGS

FIGS. 4 and 5 are views explaining the operation of the screw locking member in the cervical plating system shown in FIG. 1, in which FIG. 4 shows the screw locking member in the first position, and FIG. 5 shows the screw locking member in the second position; and FIGS. 6 and 7 are views explaining the operation of the screw position fixing member in the cervical plating system shown in FIG. 1, in which FIG. 6 shows the screw position fixing member and the screw locking member before the fastening screw is fastened to a vertebra, and FIG. 7 shows the screw position fixing member and the screw locking member after the fastening screw is fastened to a vertebra.

DETAILED DESCRIPTION OF THE INVENTION

Advantages of the present invention and the operation thereof as well as objects to be realized by the present invention can be more apparent from the following description taken in conjunction with the accompanying drawings, in which exemplary embodiments of the invention are shown.

Reference will now be made in detail to various embodiments of the present invention, examples of which are illustrated in the accompanying drawings and described below. In the following description of the present invention, detailed descriptions of known functions and components incorporated herein will be omitted when it may make the subject matter of the present invention rather unclear.

Figure 1:
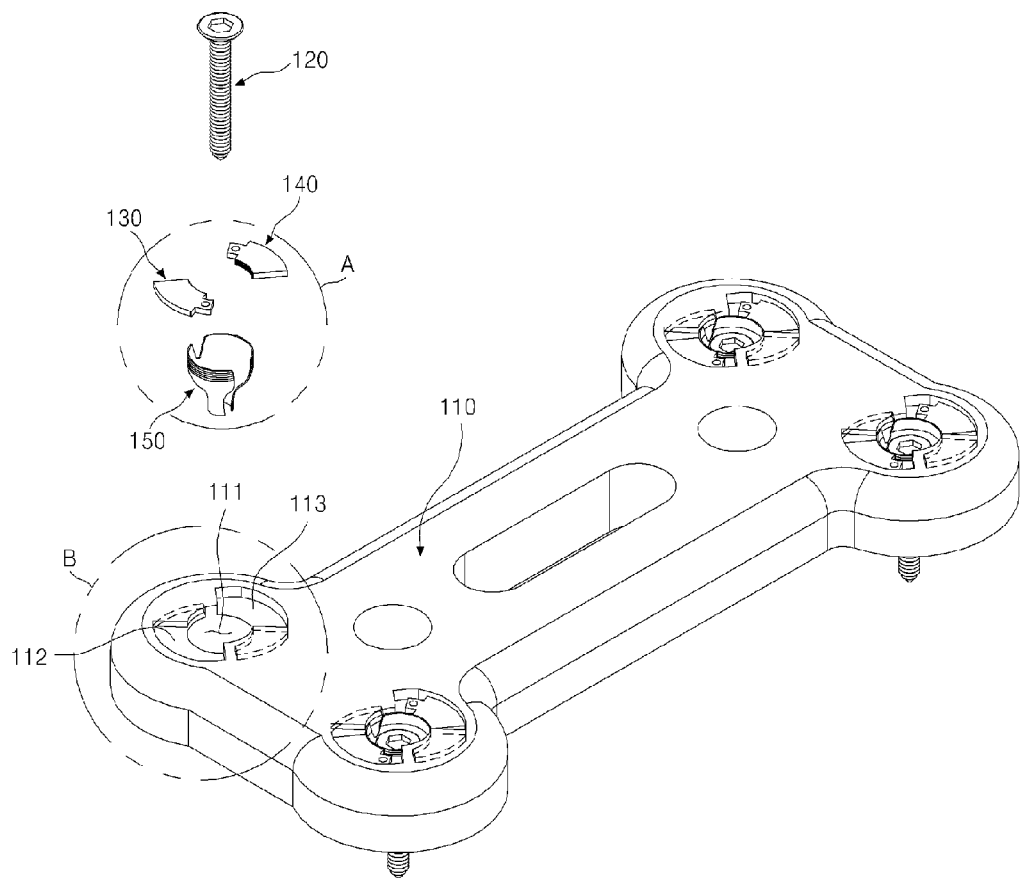
FIG. 1 is a perspective view showing a cervical plating system according to an exemplary embodiment of the invention.

FIG. 1 is a perspective view showing a cervical plating system according to an exemplary embodiment of the invention.

Referring to FIG. 1, the cervical plating system 100 of this embodiment includes a cervical plate 110, fastening screws 120, and screw locking members 130 and 140. The cervical plating system 100 of this embodiment also includes screw position fixing members 150.

The cervical plate 110 serves to support two or more vertebrae by connecting them to each other in an operation that is performed to fuse upper and lower vertebrae, and is fixed to the two or more vertebrae via the fastening screws 120. For this, the cervical plate 110 is provided generally in the shape of a plate, and has defined therein a plurality of fastening holes 111 into which the fastening screws 120 are fitted. The cervical plate 110 shown in FIG. 1 is designed to support two vertebrae by connecting them to each other, and has a total of 4 fastening holes 111 in corners thereof. However, the number of fastening holes 111 in the cervical plate 110 can be suitably changed. In an example, it is preferred that the cervical plate for supporting three vertebrae by connecting them to each other typically have a total of 6 fastening holes. In addition, the cervical plate 110 is provided substantially in the form of a quadrangular plate, and its size can vary depending on the number of vertebrae to which the cervical plate 110 is fastened.

The fastening screws 120 are components for fastening the cervical plate 110 to two or more vertebrae. An operator can fixedly fasten the cervical plate 110 to two or more vertebrae by fitting the fastening screws 120 into the fastening holes 111 in the cervical plate 110, as shown in FIG. 1, and then turning the fastening screws 120 using a tool such as a driver. In this embodiment, a total of 4 fastening screws 120 are used. However, the type, the shape, and the like of the fastening screws 120 are not limited to those disclosed in this embodiment, but can be suitably varied.

Figure 2:
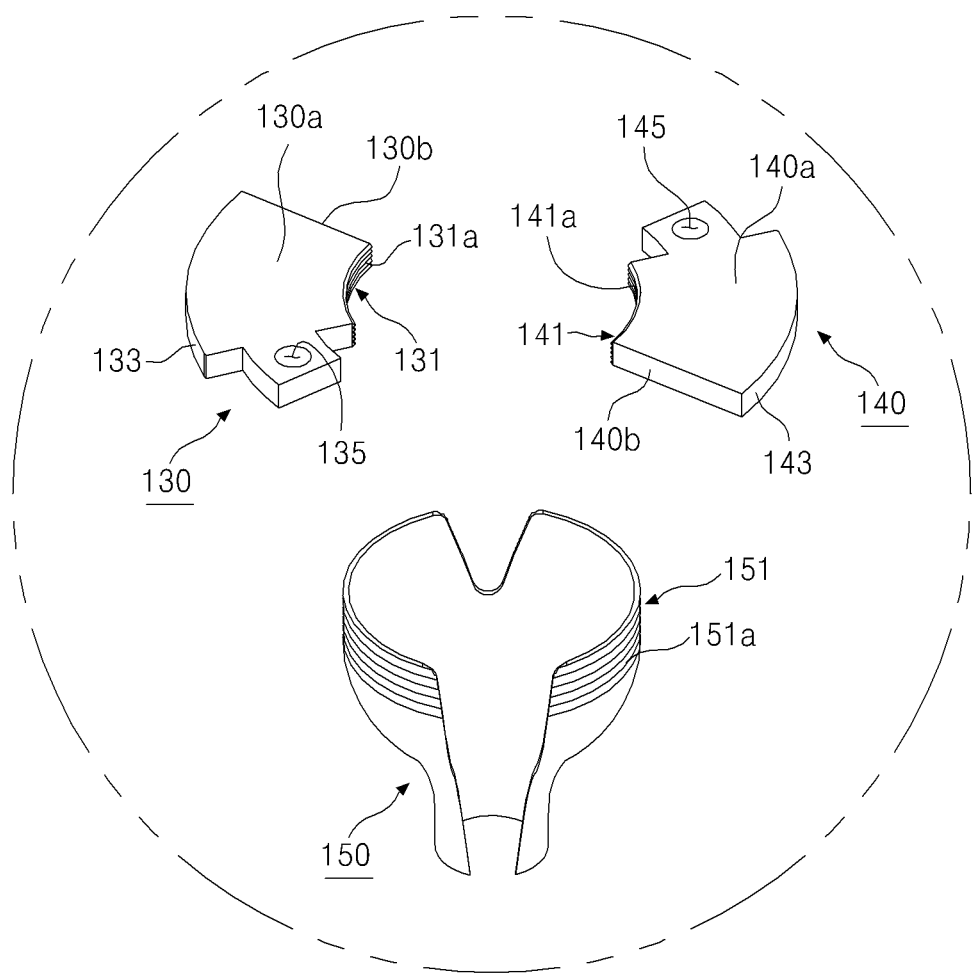
FIG. 2 is an enlarged view of the area "A" in FIG. 1.
Figure 3:
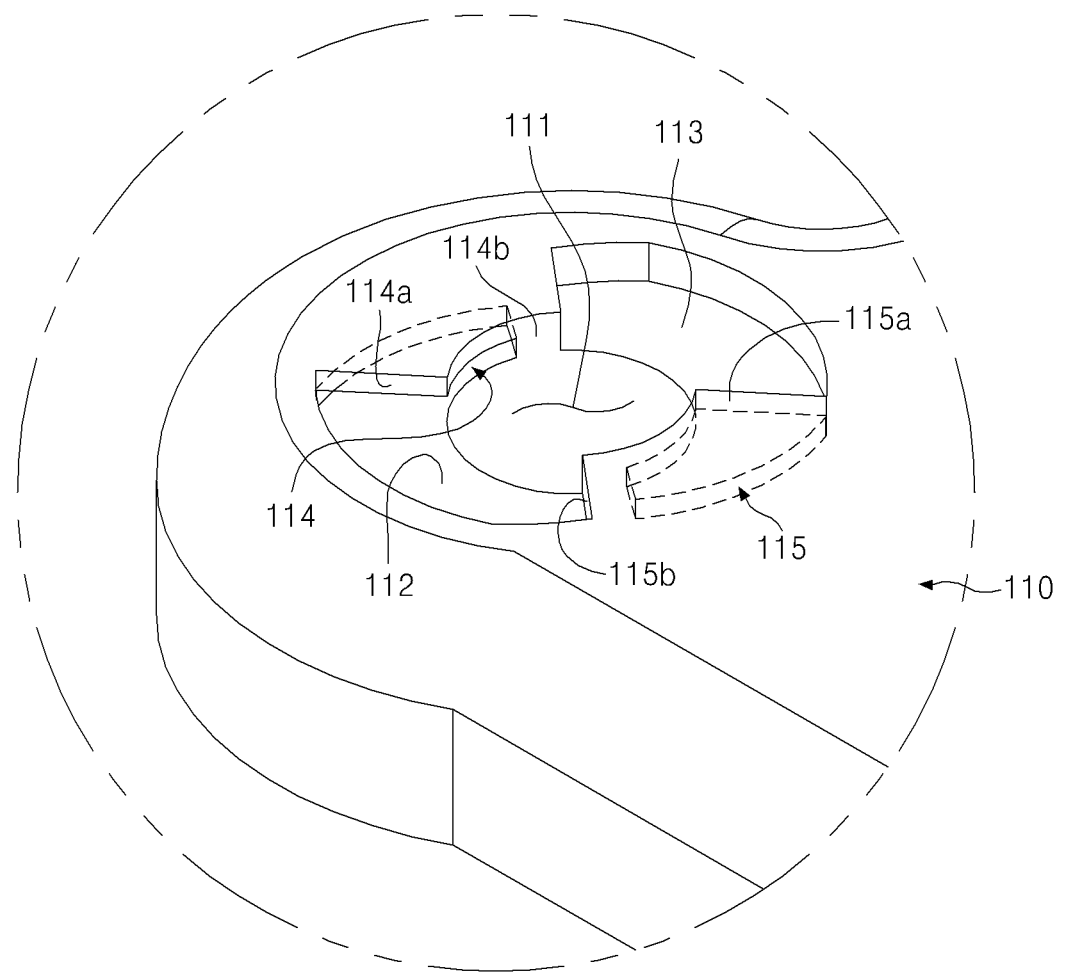
FIG. 3 is an enlarged view of the area "B" in FIG. 1.
Figure 4:
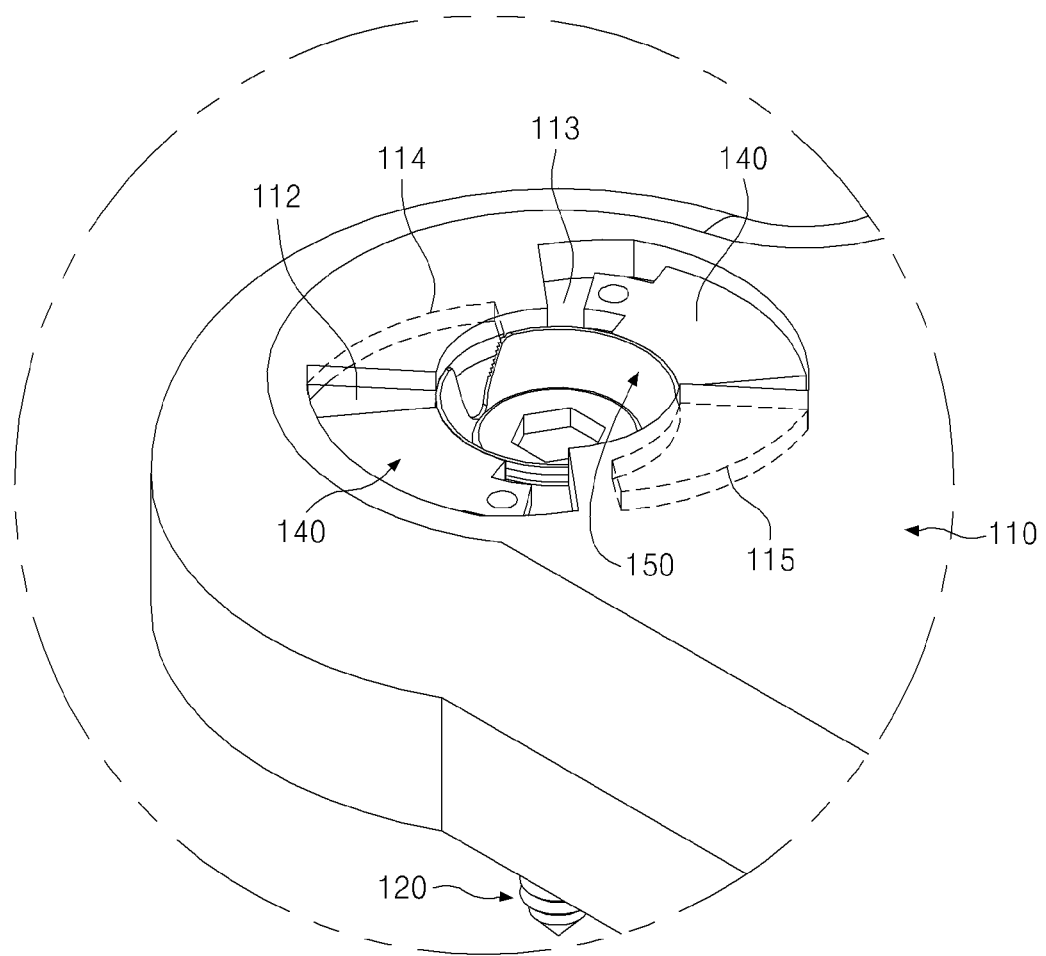
Figure 5:
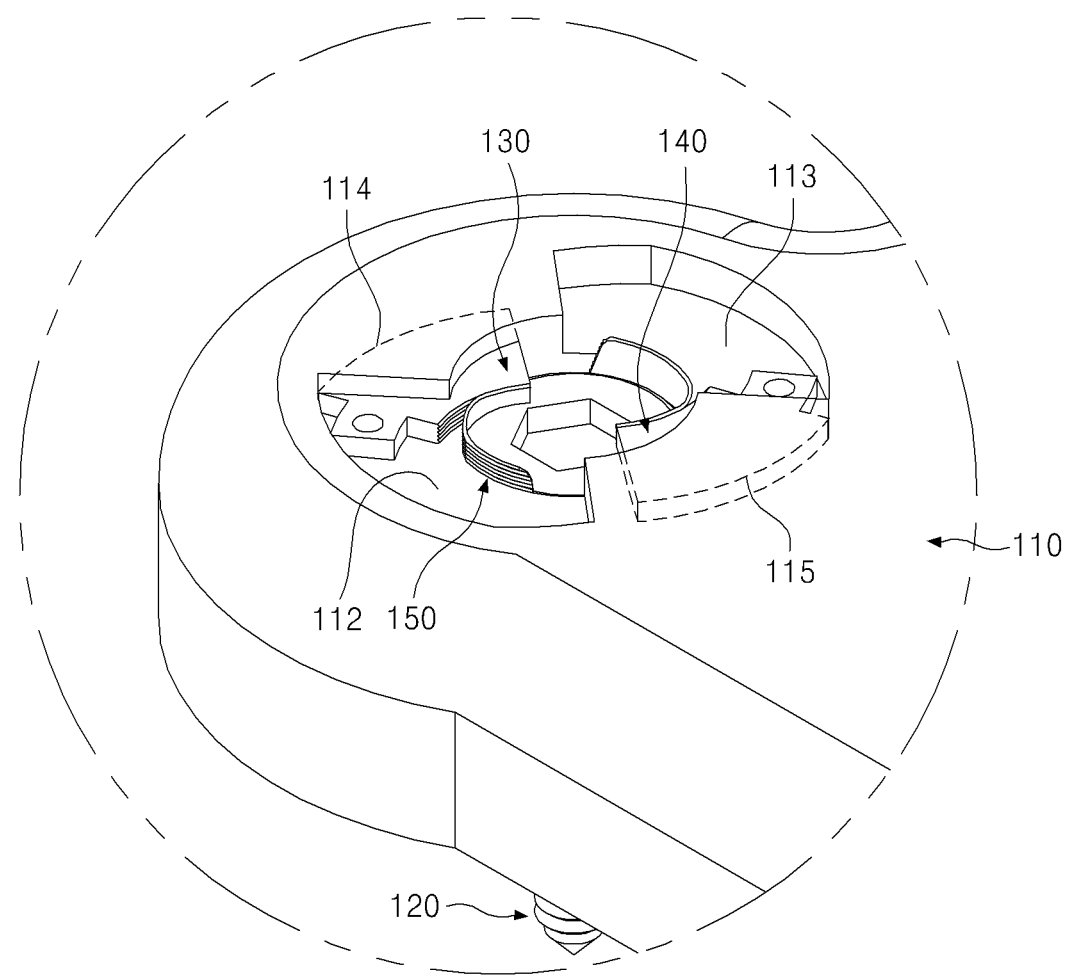

FIG. 2 is an enlarged view of the area "A" in FIG. 1, and FIG. 3 is an enlarged view of the area "B" in FIG. 1. FIGS. 4 and 5 are views explaining the operation of the screw locking member in the cervical plating system shown in FIG. 1, in which FIG. 4 shows the screw locking member in the first position, and FIG. 5 shows the screw locking member in the second position.

Referring to FIGS. 1 to 5, the screw locking members 130 and 140 are provided in the form of a plate having a predetermined thickness, and are disposed adjacent to the fastening hole 111 in the cervical plate 110. The screw locking members 130 and 140 are provided along the circumference of the fastening hole 111 in the cervical plate 110, such that they can rotate between first and second positions. Here, as shown in FIG. 4, the "first position" refers to the position in which the screw locking members 130 and 140 do not close the fastening hole 111 in the cervical plate 110, as shown in FIG. 4, and "second position" refers to the position in which the screw locking members 130 and 140 at least partially close the fastening hole 111 in the cervical plate 110, as shown in FIG. 5. In other words, the screw locking members 130 and 140 do not overlap the fastening hole 111 in the cervical plate 110 in the first position, whereas the screw locking members 130 and 140 partially overlap the fastening hole 111 in the cervical plate 110 in the second position.

Consequently, the cervical plating system 100 of this embodiment can prevent the fastening screw 120 from being dislodged from the cervical plate 110 in the state in which the cervical plating system 100 is implanted to the human body. In particular, since an additional screw is not used unlike the related art, it can ensure high reliability in preventing the fastening screw 120 from being dislodged.

In this embodiment, the screw locking members 130 and 140 are provided as a pair of screw locking members that oppose each other. That is, the screw locking members 130 and 140 include the first screw locking member 130 and the second screw locking member 140 in order to more securely close the fastening hole 111 in the cervical plate 110 in the second position and realize stable coupling to the screw position fixing member 150, which will be described later, and a more effective operation mechanism associated with the screw position fixing member 150. However, irrespective of such merits, the number of screw locking members 130 and 140 can be selected to be different from that of this embodiment. The operator can turn the screw locking members 130 and 140 from the first position to the second position using a fine tool such as a driver. For this, as shown in FIG. 2, a driver recess 135 can be formed in the upper surface of the screw locking member 130, and a driver recess 145 can be formed in the upper surface of the screw locking member 140.

In addition, the screw locking members 130 and 140 have the inner circumferential surfaces 131 and 141 with a predetermined curvature. The inner circumferential surfaces 131 and 141 are the portions that are intended to be coupled to the screw position fixing member 150, which will be described later. Thread lines 131a and 141a are formed in the inner circumferential surfaces 131 and 141, extending along the circumference. Here, it is preferred that the curvature of the inner circumferential surfaces 131 and 141 of the screw locking members 130 and 140 be substantially the same as that of the fastening hole 111 in the cervical plate 110 for the purpose of the effective operation mechanism of the screw locking members 130 and 140 and the screw position fixing member 150. For reference, in this embodiment, the outer circumferential surfaces 133 and 143 of the screw locking members 130 and 140 are substantially concentric with the inner circumferential surfaces 131 and 141. Thus, in this embodiment, the screw locking members 130 and 140 are configured such that they have a constant width along the circumference thereof.

Referring to FIGS. 1 to 5, in the cervical plating system 100 of this embodiment, the cervical plate 110 also has guide recesses 112 and 113 and fitting recesses 114 and 115 formed around the fasting hole 111 thereof.

The guide recesses 112 and 113 are depressed with respect to the upper portion of the cervical plate 110 such that they can guide the rotation of the screw locking members 130 and 140. The guide recesses 112 and 113 are formed in a predetermined range along the circumference of the fastening hole 111 in the cervical plate 110, that is, in the circumferential direction of the fastening hole 111. In addition, the guide recesses 112 and 113 are formed with a predetermined width along the circumference of the fastening hole 111 in the cervical plate 110. The guide recesses 112 and 113 are divided into the first and second guide recesses 112 and 113, which oppose each other such that they correspond to a pair of the screw locking members 130 and 140. Specifically, the first screw locking member 130 is disposed in the first guide recess 113a, and the second screw locking member 140 is disposed in the second guide recess 113b. Here, it is preferred that the depth to which the guide recesses 112 and 113 are depressed be set to be greater than the thickness of the screw locking members 130 and 140. Thanks to the guide recesses 112 and 113, the screw locking members 130 and 140 can stably and reliably rotate between the first and second positions along the circumference of the fastening hole 111 in the cervical plate 110.

As shown in FIG. 5, the screw locking members 130 and 140 are fitted into the fitting recesses 114 and 115 so that they partially overlap with fastening hole 111 in the cervical plate 110. Specifically, the screw locking members 130 and 140 are fitted into the fitting recesses 114 and 115 in the second position. Here, the screw locking members 130 and 140 are arranged such that they partially overlap the fastening hole 111. The fitting recesses 114 and 115 extend from the guide recesses 112 and 113 along the circumference of the fastening hole 111 in the cervical plate 110. Specifically, in the fitting recesses 114 and 115, the first fitting recess 114 extends from the first guide recess 112, and the second fitting recess 115 extends from the second guide recess 113. The fitting recesses 114 and 115 extending from the guide recesses 112 and 113 are configured such that they are depressed in the lateral direction of the guide recesses 112 and 113, that is, in the direction of the plane of the cervical plate 110. Thus, the fitting recesses 114 and 115 extend into the space that is defined, in the second position, by the upper walls 114a and 115a, which cover the upper surfaces 130a and 140a of the screw locking members 130 and 140, and the side walls 114b and 115b, which cover the side surfaces 130b and 140b of the screw locking members 130 and 140. Here, unlike the guide recesses 112 and 113 having a predetermined width along the circumference of the fastening hole 111, the fitting recesses 114 and 115 are configured such that their width gradually decreases along the circumference of the fastening hole 111 in the direction away from the guide recesses 112 and 113. This is for the purpose of ensuring that the screw locking members 130 and 140 partially overlap the fastening hole 111 in the second position, in which they are fitted into the fitting recesses 114 and 115. In the meantime, it is preferred that the screw locking members 130 and 140 be fitted into the fitting recesses 114 and 115 via interference fitting so that they can be fixed in the second position.

Figure 6:
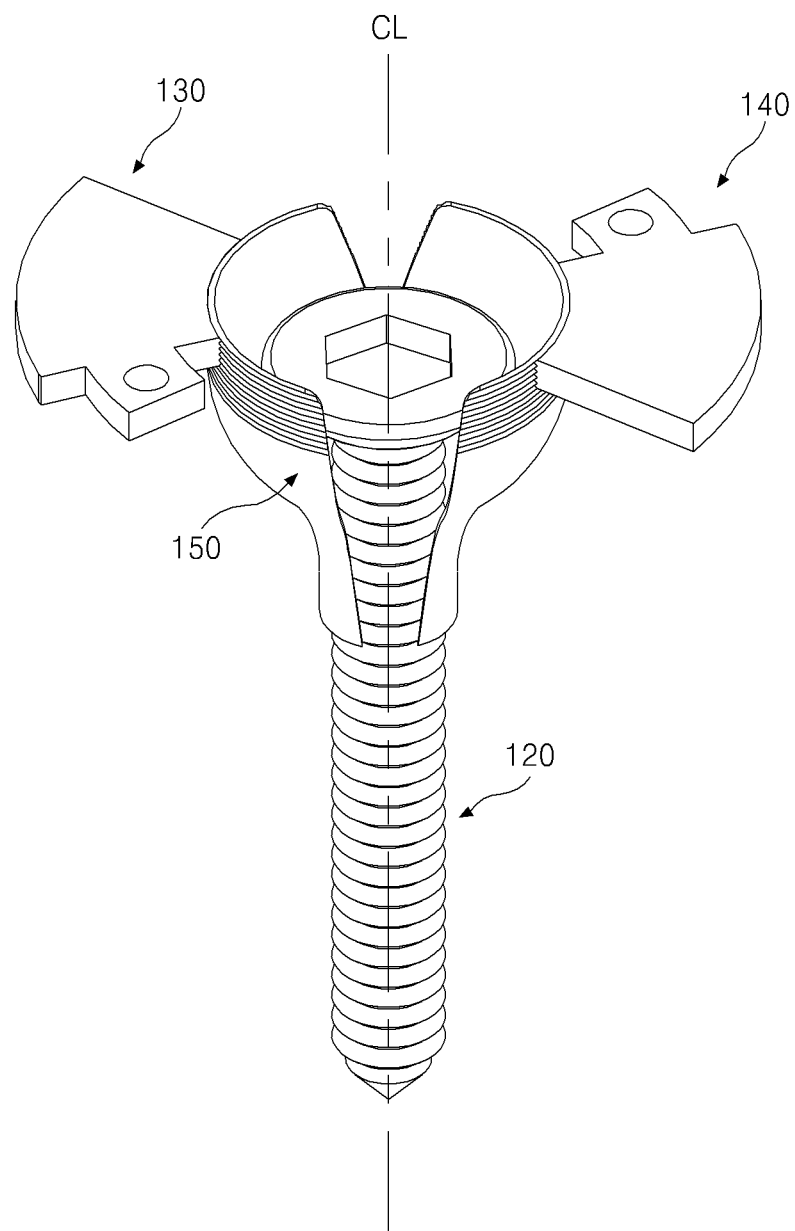
Figure 7:
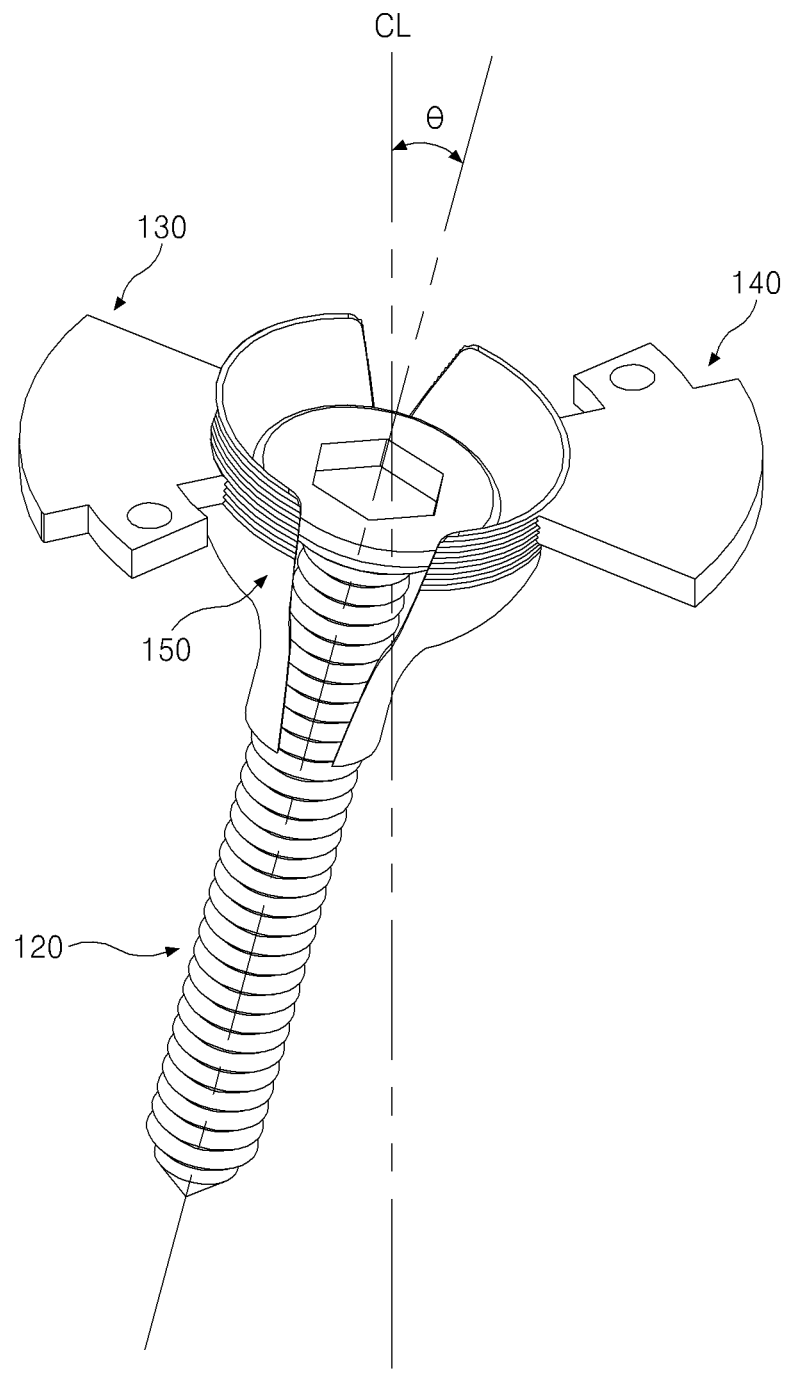

FIGS. 6 and 7 are views explaining the operation of the screw position fixing member in the cervical plating system shown in FIG. 1, in which FIG. 6 shows the screw position fixing member and the screw locking member before the fastening screw is fastened to a vertebra, and FIG. 7 shows the screw position fixing member and the screw locking member after the fastening screw is fastened to a vertebra.

Referring to FIGS. 1 to 7, the screw position fixing member 150 is fitted into the fastening hole 111 such that it surrounds and fixes the fastening screw 120, and is coupled to the screw locking members 130 and 140. The screw position fixing member 150 can securely fix the position or posture of the fastening screw 120, which is fastened to a vertebra, thereby preventing the phenomenon in which the fastening screw 120 is shaken since the fastening between the vertebra and the fastening screw 120 becomes loose by the influence of vibration from the voice of a patient or the like after an operation.

The screw position fixing member 150 is configured such that it can move within a predetermined range in the state in which it is fitted into the fastening hole 111 before the fastening screw 120 is fastened to the vertebra. For this, the upper end of the screw position fixing member 150 has a width (or diameter) greater than that of the fastening hole 111 such that it can overlap the portion of the cervical plate 110 around the fastening hole 111, whereas the other portion of the screw position fixing member 150 has a width (or diameter) smaller than that of the fastening hole 111 such that it can move within a predetermined range inside the fastening hole 111. Specifically, as shown in FIGS. 6 and 7, the screw position fixing member 150 can have the form of a funnel, with a width thereof gradually decreasing in the direction toward the bottom, such that it surrounds the fastening screw 120. In addition, a portion of the sidewall of the funnel is cut open. However, the screw position fixing member 150 is not limited to the funnel shape disclosed in this embodiment, but can be, of course, modified into various shapes, each of which is fitted into the fastening hole 111 and surrounds the fastening screw 120. In the meantime, it is preferred that the screw position fixing member 150 have a relatively smaller thickness compared to the foregoing screw locking members 130 and 140 such that it can be deformed to a predetermined extent.

In the state in which the screw position fixing member 150 is fitted into the fastening hole 111 in the cervical plate 110, it is coupled with the screw locking members 130 and 140. Specifically, the outer circumferential surface 151 of the upper end of the screw position fixing member 150 and the inner circumferential surfaces 131 and 141 of the screw locking members 130 and 140 are coupled to each other. The screw position fixing member 150 has the outer circumferential surface 151 coupled to the inner circumferential surfaces 131 and 141 of the screw locking members 130 and 140. Here, it is preferred that the screw position fixing member 150 be coupled to the screw locking members 130 and 140 via screw engagement such that a secure coupling can be realized without hindering the above-described rotation of the screw locking members 130 and 140. For this, the screw position fixing member 150 has threads 151a in the outer circumferential surface 151 of the upper end thereof. The threads 151a correspond to the thread lines 131a and 141a formed in the inner circumferential surfaces 131 and 141 of the screw locking members 130 and 140.

In general, in the process of fixing the cervical plate 110 to vertebrae, the fastening screw 120 is not perpendicular to the vertebrae, but, as shown in FIG. 7, inclined at a predetermined fastening angle θ (about 15°) with respect to the center line CL of the fastening hole 111. Here, the screw position fixing member 150 can be inclined along with the fastening screw 120 at the fastening angle (θ) of the fastening screw 120, since it can move inside the fastening hole 111 before the fastening screw 120 is fastened to the vertebra. Specifically, before the fastening hole 120 is fastened to the vertebra, the screw position fixing member 150 can be arranged parallel to the center line CL of the fastening hole 111, as shown in FIG. 6. In contrast, the screw position fixing member 150 can be moved along with the fastening screw 120 so that it is arranged at an incline when the fastening screw 120 is fastened as being inclined at the fastening angle θ, as shown in FIG. 7. The arrangement of the screw position fixing member 150 can be fixed via coupling of the screw position fixing member 150 to the screw locking members 130 and 140, which are mounted on the cervical plate 110 after the fastening screw 120 is fastened on the vertebra. In particular, the arrangement of the screw position fixing member 150 can be securely fixed and maintained as the screw locking members 130 and 140 are rotated from the first position to the second position (see FIG. 5). In other words, the screw position fixing member 150 can be fixedly inclined inside the fastening hole 111 at the fastening angle θ of the fastening screw 120 after the fastening screw 120 is fastened to the vertebra.

Consequently, the screw position fixing member 150 can securely fix the position or posture of the fastening screw 120 even if the fastening screw 120 is fastened at an incline, thereby preventing the phenomenon in which the fastening between the vertebra and the screw becomes loose by the influence of vibration from the voice of the patient or the like and the fastening screw 120 becomes loose after the operation.

The foregoing descriptions of specific exemplary embodiments of the present invention have been presented for the purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

What is claimed is:

1. A cervical plating system for fixedly connecting two or more vertebrae to each other, comprising:
   a cervical plate having a fastening hole, the fastening hole penetrating the cervical plate;
   a fastening screw fitted into the fastening hole in the cervical plate; and
   a screw locking member disposed in a recess formed in the cervical plate, the screw locking member being in a form of a plate, wherein the screw locking member is rotatable along a circumference of the fastening hole between a first position, in which the screw locking member remains inside the recess to open the fastening hole, and a second position, in which the screw locking member protrudes toward the fastening hole to at least partially close the fastening hole, the first and second positions being positioned at a same level with respect to an upper surface of the cervical plate.

2. The cervical plating system of claim 1, further comprising a screw position fixing member fitted into the fastening hole, wherein the screw position fixing member surrounds and fixes the fastening screw, and is coupled to the screw locking member.

3. The cervical plating system of claim 1, wherein the recess includes a guide recess depressed with respect to the upper surface of the cervical plate, the guide recess being formed along the circumference of the fastening hole to guide a rotational movement of the screw locking member.

4. The cervical plating system of claim 2, wherein the recess includes a guide recess depressed with respect to the upper surface of the cervical plate, the guide recess being formed along the circumference of the fastening hole to guide a rotational movement of the screw locking member.

5. The cervical plating system of claim 3, wherein the recess further includes a fitting recess therein, the screw locking member being fitted into the fitting recess such that a portion of the screw locking member overlaps the fastening hole.

6. The cervical plating system of claim 4, wherein the recess further includes a fitting recess therein, the screw locking member being fitted into the fitting recess such that a portion of the screw locking member overlaps the fastening hole.

7. The cervical plating system of claim 5, wherein the fitting recess extends from the guide recess along the circumference of the fastening hole, and is depressed in a lateral direction.

8. The cervical plating system of claim 6, wherein the fitting recess extends from the guide recess along the circumference of the fastening hole, and is depressed in a lateral direction.

9. The cervical plating system of claim 7, wherein the guide recess has a width that is constant along the circumference of the fastening hole, and the fitting recess has a width that gradually decreases in a direction away from the guide recess along the circumference of the fastening hole.

10. The cervical plating system of claim 8, wherein the guide recess has a width that is constant along the circumference of the fastening hole, and the fitting recess has a width that gradually decreases in a direction away from the guide recess along the circumference of the fastening hole.

11. The cervical plating system of claim 1, wherein the screw locking member comprises a pair of screw locking members, which oppose each other.

12. The cervical plating system of claim 2, wherein the screw locking member comprises a pair of screw locking members, which oppose each other.

13. The cervical plating system of claim 1, wherein the screw locking member has an inner circumferential surface with a predetermined curvature.

14. The cervical plating system of claim 2, wherein the screw locking member has an inner circumferential surface with a predetermined curvature.

15. The cervical plating system of claim 1, wherein the screw locking member has a driver socket in an upper surface thereof, such that a driver for rotating the screw locking member fits into the driver socket.

16. The cervical plating system of claim 2, wherein the screw locking member has a driver socket in an upper surface thereof, such that a driver for rotating the screw locking member fits into the driver socket.

17. The cervical plating system of claim 2, wherein the screw position fixing member is movable within a predetermined range in a state in which the screw position fixing member is fitted into the fastening hole before the fastening screw is fastened to a vertebra.

18. The cervical plating system of claim 17, wherein the screw position fixing member is arranged and fixed at an incline in the fastening hole according to a fastening angle of the fastening screw after the fastening screw is fastened to the vertebra.

19. The cervical plating system of claim 17, wherein the screw position fixing member is shaped as a funnel, with a width thereof gradually decreasing toward bottom, and a portion of a sidewall thereof being open.

20. The cervical plating system of claim 2, wherein the screw locking member has an inner circumferential surface with a predetermined curvature, and the screw position fixing member has an outer circumferential surface that couples with the inner circumferential surface of the screw locking member.

21. The cervical plating system of claim 17, wherein the screw locking member has an inner circumferential surface with a predetermined curvature, and the screw position fixing member has an outer circumferential surface that couples with the inner circumferential surface of the screw locking member.

22. The cervical plating system of claim 20, wherein the inner circumferential surface of the screw locking member and the outer circumferential surface of the screw position fixing member are coupled to each other via screw engagement.

23. The cervical plating system of claim 21, wherein the inner circumferential surface of the screw locking member and the outer circumferential surface of the screw position fixing member are coupled to each other via screw engagement.

* * * * *